US00PP20257P2

(12) United States Plant Patent
Gutter

(10) Patent No.: US PP20,257 P2
(45) Date of Patent: Sep. 1, 2009

(54) ***SAXIFRAGA* PLANT NAMED 'ROCKLARWHI'**

(50) Latin Name: *Saxifraga×arendsii*
Varietal Denomination: Rocklarwhi

(75) Inventor: Martien Everett Gutter, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 12/148,301

(22) Filed: Apr. 18, 2008

(51) Int. Cl.
*A01H 5/00* (2006.01)

(52) U.S. Cl. ..... Plt./263.1

(58) Field of Classification Search ..... Plt./263.1, Plt./226

See application file for complete search history.

*Primary Examiner*—June Hwu
(74) *Attorney, Agent, or Firm*—S. Matthew Edwards

(57) ABSTRACT

A new *Saxifraga* plant named 'Rocklarwhi,' particularly distinguished by its completely white flower color, very big flower size, early flowering, and compact plant habit.

1 Drawing Sheet

Latin name of the genus and species of the plant claimed: *Saxifraga×arendsii.*

Varietal denomination: 'Rocklarwhi'.

BACKGROUND OF THE NEW PLANT

The present invention comprises a new distinct cultivar of *Saxifraga,* botanically known as *Saxifraga×arendsii.*

The new *Saxifraga* is a product of a planned breeding program conducted in Enkhuizen, Netherlands. The new *Saxifraga* cultivar has a compact plant habit, a pure white flower color, very large flowers, and is very early flowering.

The new *Saxifraga* is propagated by cuttings resulting from a single seedling. This seedling originated from an open pollination of a white flowering selection identified as number 'D571' (not patented). This pollination took place in April 2003 in Enkhuizen, Netherlands. The seeds were sown in August 2003. The seedling was selected in March 2004 in Enkhuizen.

The present cultivar has been repeatedly asexually reproduced by cuttings in Enkhuizen, Netherlands, since 2004. The distinctive characteristics of this new *Saxifraga* are stable and reproduced true to type in successive generations of asexual reproduction. It takes 21 to 27 weeks to produce a finished plant, depending on the temperature.

The new *Saxifraga* plant is a perennial in all climatic zones in the US.

DESCRIPTION OF THE DRAWING

The new *Saxifraga* plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new *Saxifraga.* The data which defines these characteristics were collected from asexual reproductions carried out in Enkhuizen, Netherlands. The plant history was taken on 28 week old plants. The instant plant was grown in an 11 cm container in a plastic tunnel.

Color references are primarily to the RHS Colour Chart of The Royal Horticultural Society of London, edition 2001.

Plants of the new *Saxifraga* differ primarily from the plants of the originator 'D571' in the following characteristics:

Plants of the new variety have completely white flowers and a compact growth habit, whereas plants of 'D571' have white flowers with pink edges, and a loose growth habit. The flowers of the new variety have almost double the size of the flowers of 'D571.' Plants of the new variety start flowering two weeks earlier than the plants of 'D571'.

TABLE 1

DIFFERENCES BETWEEN THE NEW CULTIVAR 'ROCKLARWHI' AND A SIMILAR CULTIVAR

| | 'Rocklarwhi' | 'Rockwhite.' (U.S. Ser. No. 1,010) |
|---|---|---|
| Flower color | Whole flower is lighter than 155C | Lighter than 155C, 63A on apex and round central vein |
| Flower petal length | 1.2-1.4 cm | 0.7-1.0 cm |
| Time of flowering | 21-27 weeks after cutting | 23-29 weeks after cutting |

The plant:

*Classification-Botanical.*—*Saxifraga×arendsii.*

Parentage:

*Originator selection.*—'D571' (not patented).

Propagation:

*Type of cutting.*—Terminal cuttings.

*Time to initiate roots.*—12–14 days at 18° C.

*Time to produce a rooted cutting.*—4 weeks.

*Root description.*—Fine, fibrous and white in color.

Plant description:

*General appearance.*—Makes mats of rosettes. Each rosette develops. Several short branches, and one or more branched flower stems.

*Growth and branching habit.*—Freely branching habit, freely flowering, vigorous.
*Plant height.*—14 cm.
*Plant spread.*—18 cm.

Lateral branches:
*Length.*—2–4 cm.
*Diameter.*—1.2 mm.
*Texture.*—Smooth; slightly pubescent with long hairs: 2–3 mm.
*Internode length.*—2–5 mm.
*Color.*—145C.

The foliage:
*Arrangement.*—Alternate.
*Shape of blade.*—Five-lobed.
*Length, mature leaves.*—1.0–1.3 cm.
*Width, mature leaves.*—0.8–1.1 cm.
*Apex.*—Acute.
*Base.*—Acute.
*Margin.*—Entire.
*Texture.*—Smooth, slightly pubescent.
*Venation pattern.*—Palmate.
*Color of upper surface.*—145A.
*Color of lower surface.*—144A.
*Venation, upper surface.*—145B.
*Venation, lower surface.*—144A.

The petiole:
*Length.*—1.2–1.7 cm.
*Width.*—1 mm.
*Color upper surface.*—144A.
*Color lower surface.*—144B.
*Texture.*—Smooth; slightly pubescent.

The flower:
*Inflorescence type.*—Each rosette develops 1–3 branched flower stems.
*Flower type.*—Single, solitary; symmetry: radial symmetric.
*Number of branches per flower stem.*—2–5.
*Number of flowers and flower buds per flower stem.*—2–15.
*Length flower stem.*—4–9 cm.
*Flower position.*—At top of branch.
*Fragrance.*—Absent.
*Flowering season.*—Spring.
*Flower diameter.*—1.8–2.6 cm.
*Lastingness of the bloom.*—40–50 days.
*Lastingness of an individual flower.*—4–8 days.

Flower buds:
*Bud length* (*at stage of showing color*).—3 mm.
*Bud diameter.*—3 mm.
*Bud shape.*—Orbicular.
*Texture.*—Smooth; pubescent.
*Color, just before opening.*—155B.

Petals:
*Quantity.*—5 per flower, imbricate.
*Shape.*—Orbicular.
*Apex.*—Rounded to acuminate.
*Base.*—Shortly attenuate.
*Length.*—12–14 mm.
*Width.*—8–11 mm.
*Margin.*—Entire.
*Texture.*—Smooth.
*Color upper surface.*—Young flower—155D. Old flower—Lighter than 155C.
*Color lower surface.*—Young flower—155D. Old flower—155C.
*Venation pattern.*—Bowed.
*Venation upper surface.*—155A.
*Venation lower surface.*—155B.

Sepals:
*Quantity.*—0.5 per flower.
*Shape.*—Ovate.
*Apex.*—Acute.
*Margin.*—Entire.
*Length.*—3–4 mm.
*Width.*—2.5–3.5 mm.
*Color upper surface.*—146B.
*Color lower surface.*—146C.
*Texture upper surface.*—Smooth; slightly pubescent.
*Texture lower surface.*—Smooth, glabrous.

Peduncles:
*Length.*—0.5–0.9 cm.
*Diameter.*—1 mm.
*Color.*—144A.
*Texture.*—Smooth; pubescent.

Reproductive organs:
*Androecium.*—
*Stamen number.*—10, not fused.
*Filament length.*—3–5 mm.
*Filament shape.*—Threadlike.
*Filament color.*—154B.
*Anther shape.*—Bi-lobed.
*Anther length.*—1.5 mm.
*Anther color.*—149A.
*Color of pollen.*—2A.
*Amount of pollen.*—Normal.
*Gynoecium.*—
*Pistil number.*—2.
*Pistil length.*—3–4 mm.
*Stigma color.*—155A.
*Style color.*—1B.
*Ovary color.*—150A.

Seed development: Seed development has not been observed to date.

Disease/pest resistance: No disease/pest resistance has been observed to date.

What is claimed is:

1. A new and distinct variety of *Saxifraga* plant named 'Rocklarwhi,' as substantially illustrated and described herein.

* * * * *

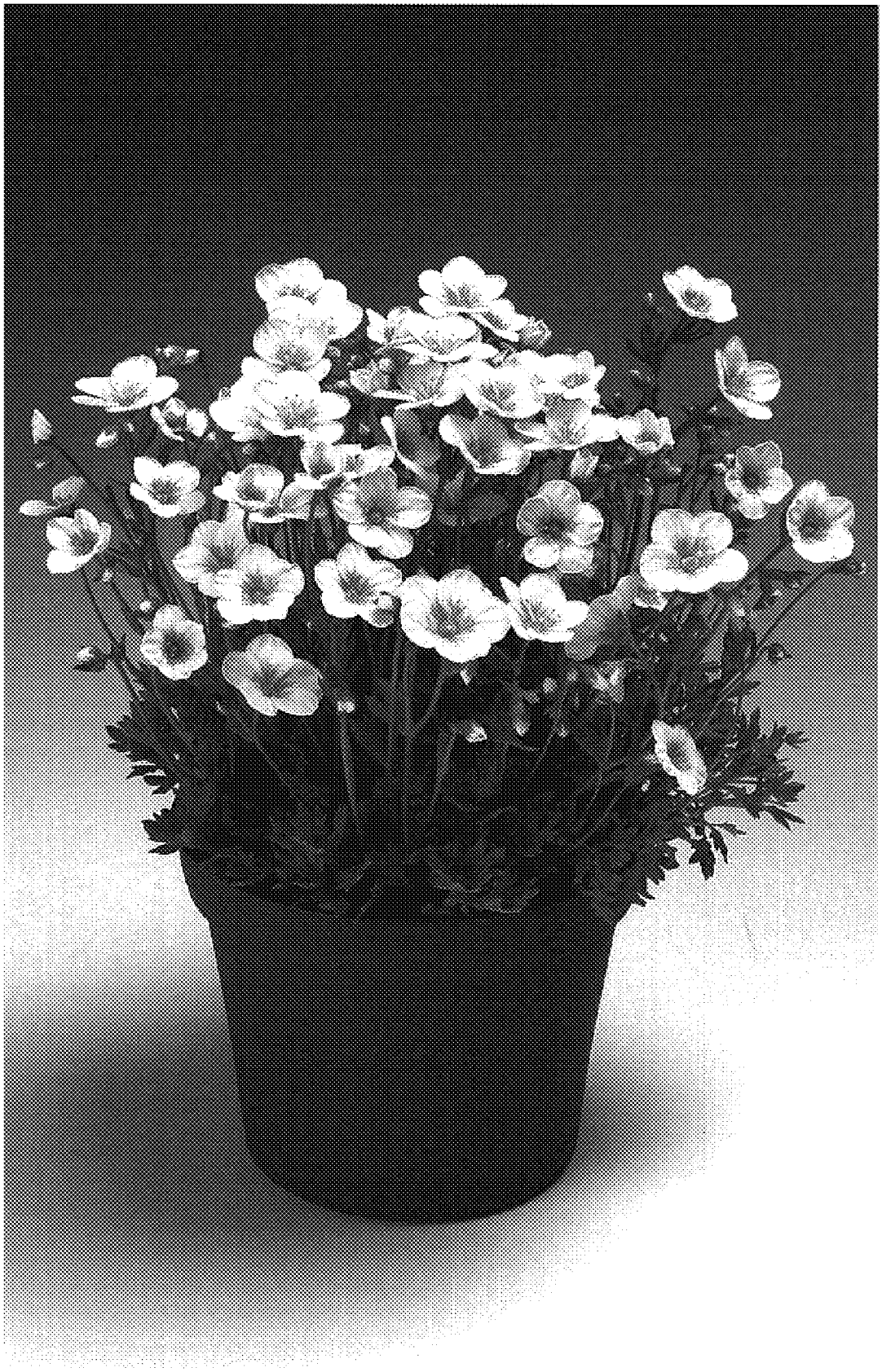

UNITED STATES PATENT AND TRADEMARK OFFICE

CERTIFICATE OF CORRECTION

PATENT NO. : PP 20,257 P2
APPLICATION NO. : 12/148301
DATED : September 1, 2009
INVENTOR(S) : Gutter It is certified that error appears in the above-identified patent and that said Letters Patent is hereby corrected as shown below:

At column 2, in Table 1, delete "U.S. Ser. No. 1,010" and insert therefor --U.S. Patent No. 19,010--

At column 2, line 41, delete "." after "develops" and delete "Several" and insert therefor --several--

At column 4, under "Sepals:" and following "Quantity-", delete "0.5" and insert therefor --5--

Signed and Sealed this

Thirteenth Day of October, 2009

David J. Kappos

David J. Kappos
*Director of the United States Patent and Trademark Office*